United States Patent [19]

Hertel

[11] Patent Number: 4,526,988
[45] Date of Patent: Jul. 2, 1985

[54] DIFLUORO ANTIVIRALS AND INTERMEDIATE THEREFOR

[75] Inventor: Larry W. Hertel, Indianapolis, Ind.

[73] Assignee: Eli Lilly and Company, Indianapolis, Ind.

[21] Appl. No.: 473,883

[22] Filed: Mar. 10, 1983

[51] Int. Cl.$^3$ ............................................. C07D 307/32
[52] U.S. Cl. .................................... 549/313; 536/23; 536/24; 536/26; 536/1.1
[58] Field of Search .......................................... 549/313

[56] References Cited

U.S. PATENT DOCUMENTS

| | | | |
|---|---|---|---|
| 2,359,096 | 9/1944 | Elderfield | 549/313 |
| 2,359,208 | 9/1944 | Elderfield | 549/313 |
| 4,211,773 | 7/1980 | Lopez et al. | 424/180 |
| 4,352,795 | 10/1982 | Cook | 424/180 |

FOREIGN PATENT DOCUMENTS 1362039  4/1964  France ............................ 549/313

OTHER PUBLICATIONS

DeClercq et al., *Proc. Natl. Acad. Sci. USA* 76, 2947–2951 (1979).
*J. Med. Chem.* 22, 21–24 (1979).
Howard J. Schaeffer, *American Journal of Medicine*, Jul. 1982, 4–6.
Kaufman and Heidelberger, *Science* 145, 585–586 (1964).
Prusoff, *Biochim. Biophys. Acta* 32, 295–296 (1959).
Witkowski et al., *J. Med. Chem.* 15, 1150–1154 (1972).
De Rudder and De Garilhe, *Antimicrobial Agents and Chemotherapy*, 578–584 (1965).
Penglis, *Advances in Carbohydrate Chemistry and Biochemistry* 38, 195–285 (1981).
Fox et al., *Seventh International Symposium of Medicinal Chemistry*, 1980, published by Pergamon Press (1981), pp. 27–39.
Reichman et al., *Carbohydrate Research* 42, 233–249 (1975).
Wright and Taylor, *Carbohydrate Research* 6, 347–354 (1968).
Adamson et al., *Carbohydrate Research* 18, 345–347 (1971).
Hough et al., *J. Chem. Soc. Perkin I*, 784–788 (1972).
Masamune, Sharpless et al., *J. Org. Chem.* 47, 1373–1381 (1982).
Abstract, Spring 1983 ACS Meeting at Seattle, D. E. Bergstrom.

*Primary Examiner*—Ethel G. Love
*Attorney, Agent, or Firm*—Bruce J. Barclay; Joseph A. Jones; Arthur R. Whale

[57] ABSTRACT

A 2,2-difluoro-2-desoxycarbohydrate is used to prepare antiviral nucleosides.

3 Claims, No Drawings

DIFLUORO ANTIVIRALS AND INTERMEDIATE THEREFOR

BACKGROUND OF THE INVENTION

1. Field of the Invention

This invention belongs to the field of pharmaceutical chemistry, and provides a new difluoro carbohydrate and new antiviral nucleosides prepared by coupling the new carbohydrate with appropriate bases.

2. State of the Art

It has been known for some time that antiviral drugs can be found among the general family of nucleosides. For example, 5-(2-bromovinyl)-2'-deoxyuridine is known to be a potent agent against herpes virus. DeClercq et al., *Proc. Natl. Acad. Sci. USA* 76, 2947–51 (1979). Watanabe et al. have described a number of nucleosides formed by coupling 2-fluoro-2-deoxyarabinofuranose with bases of the cytosine and thymine groups; 5-iodocytosine was their most preferred base. *J. Med. Chem.* 22, 21–24 (1979), and U.S. Pat. No. 4,211,773.

A compound which can be described as an acyclic nucleoside, 9-(2-hydroxyethoxymethyl)guanine, is a potent antiviral agent, especially useful against herpes viruses, and is the subject of a symposium in a special issue of *American Journal of Medicine,* July 1982.

Fluorinated carbohydrates have been studied before. A survey of the subject by Penglis is in *Advances in Carbohydrate Chemistry and Biochemistry* 38, 195–285 (1981). A 2,2-difluorohexose was described by Adamson et al., *Carbohydrate Research* 18, 345–47 (1971). Wright and Taylor, *Carbohydrate Research* 6, 347–54 (1968), taught the synthesis of 9-(3-deoxy-3-fluoro-α-D-arabinofuranosyl)adenine.

Recently the total synthesis of carbohydrates has become the subject of research, and a few papers have appeared. The synthesis requires stereospecific methods, and asymmetric epoxidation and asymmetric aldol reactions have been successfully used. Masamune, Sharpless et al., *J. Org. Chem.* 47, 1373–81 (1982).

SUMMARY OF THE INVENTION

The present invention provides the difluorodesoxy carbohydrate of the formula

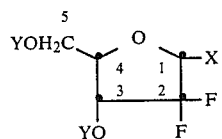

wherein X is hydroxy or a leaving group; and the Y groups independently are hydrogen or hydroxy-protecting groups.

The invention also provides the nucleosides of the formula

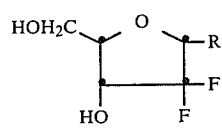

wherein R is a base of one of the formulae

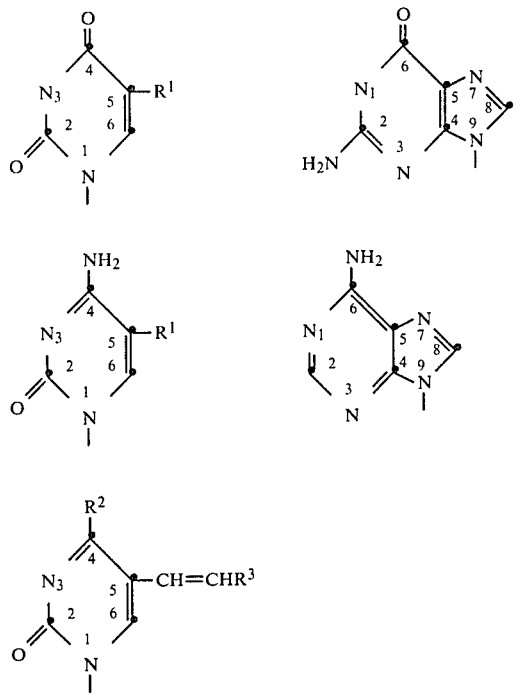

wherein
- $R^1$ is hydrogen, methyl, bromo, fluoro, chloro or iodo;
- $R^2$ is hydroxy or amino;
- $R^3$ is bromo, chloro or iodo.

The invention further comprises a process for preparing a lactone of the formula

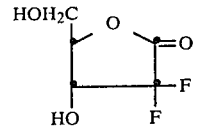

which process comprises hydrolyzing, under very mild conditions, an alkyl 3-dioxolanyl-2,2-difluoro-3-hydroxypropionate of the formula

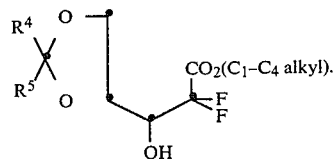

DESCRIPTION OF THE PREFERRED EMBODIMENTS

All temperatures are described in degrees Celsius in this document.

The structural drawings above do not indicate the stereochemistry of the compounds of the present invention. Compounds of all configurations are believed to be useful, and the stereochemistry of them is accordingly not a limitation. However, it is preferred that the carbohydrate have the configuration of naturally occurring ribose, as follows:

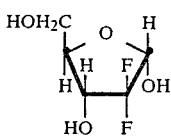

It is further preferred that the configuration of the juncture between the ribose and the base be as follows:

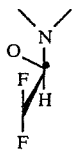

It is believed that pharmaceutical chemists are aware of the bases which are used in the synthesis of the antiviral nucleosides of the present invention, but the following specific nucleosides are mentioned to assure that every reader understands the type of antivirals which this invention makes available.

1-(5-methyl-2,4-dioxo-1H,3H-pyrimidin-1-yl)-2-desoxy-2,2-difluororibose 1-(2,4-dioxo-1H,3H-pyrimidin-1-yl)-2-desoxy-2,2-difluororibose 1-(5-bromo-2,4-dioxo-1H,3H-pyrimidin-1-yl)-2-desoxy-2,2-difluororibose 1-(5-chloro-2,4-dioxo-1H,3H-pyrimidin-1-yl)-2-desoxy-2,2-difluororibose 1-(5-iodo-2,4-dioxo-1H,3H-pyrimidin-1-yl)-2-desoxy-2,2-difluororibose 1-(4-amino-5-chloro-2-oxo-1H-pyrimidin-1-yl)-2-desoxy-2,2-difluororibose 1-(4-amino-5-bromo-2-oxo-1H-pyrimidin-1-yl)-2-desoxy-2,2-difluororibose 1-(4-amino-2-oxo-1H-pyrimidin-1-yl)-2-desoxy-2,2-difluororibose 1-(4-amino-5-iodo-2-oxo-1H-pyrimidin-1-yl)-2-desoxy-2,2-difluororibose 1-(4-amino-5-methyl-2-oxo-1H-pyrimidin-1-yl)-2-desoxy-2,2-difluororibose 1-[5-(2-bromovinyl)-4-hydroxy-2-oxo-1H-pyrimidin-1-yl]-2-desoxy-2,2-difluororibose 1-[4-amino-5-(2-bromovinyl)-2-oxo-1H-pyrimidin-1-yl]-2-desoxy-2,2-difluororibose 1-[4-amino-5-(2-iodovinyl)-2-oxo-1H-pyrimidin-1-yl]-2-desoxy-2,2-difluororibose 1-[5-(2-chlorovinyl)-4-hydroxy-2-oxo-1H-pyrimidin-1-yl]-2-desoxy-2,2-difluororibose 1-[4-hydroxy-5-(2-iodovinyl)-2-oxo-1H-pyrimidin-1-yl]-2-desoxy-2,2-difluororibose 1-[4-amino-5-(2-chlorovinyl)-2-oxo-1H-pyrimidin-1-yl]-2-desoxy-2,2-difluororibose 1-(2-amino-6-oxo-1H,9H-purin-9-yl)-2-desoxy-2,2-difluororibose 1-(6-amino-9H-purin-9-yl)-2-desoxy-2,2-difluororibose 1-(5-fluoro-2,4-dioxo-1H,3H-pyrimidin-1-yl)-2-desoxy-2,2-difluororibose 1-(2,4-dioxo-1H,3H-pyrimidin-1-yl)-2-desoxy-2,2-difluoroxylose 1-(5-bromo-2,4-dioxo-1H,3H-pyrimidin-1-yl)-2-desoxy-2,2-difluoroxylose 1-(5-chloro-2,4-dioxo-1H,3H-pyrimidin-1-yl)-2-desoxy-2,2-difluoroxylose 1-(5-iodo-2,4-dioxo-1H,3H-pyrimidin-1-yl)-2-desoxy-2,2-difluoroxylose 1-(4-amino-5-fluoro-2-oxo-1H-pyrimidin-1-yl)-2-desoxy-2,2-difluororibose 1-(4-amino-5-chloro-2-oxo-1H-pyrimidin-1-yl)-2-desoxy-2,2-difluoroxylose 1-(4-amino-2-oxo-1H-pyrimidin-1-yl)-2-desoxy-2,2-difluoroxylose 1-(4-amino-5-fluoro-2-oxo-1H-pyrimidin-1-yl)-2-desoxy-2,2-difluoroxylose 1-(4-amino-5-methyl-2-oxo-1H-pyrimidin-1-yl)-2-desoxy-2,2-difluoroxylose 1-[5-(2-bromovinyl)-4-hydroxy-2-oxo-1H-pyrimidin-1-yl]-2-desoxy-2,2-difluoroxylose 1-[4-amino-5-(2-bromovinyl)-2-oxo-1H-pyrimidin-1-yl]-2-desoxy-2,2-difluoroxylose 1-[4-amino-5-(2-iodovinyl)-2-oxo-1H-pyrimidin-1-yl]-2-desoxy-2,2-difluoroxylose 1-[5-(2-chlorovinyl)-4-hydroxy-2-oxo-1H-pyrimidin-1-yl]-2-desoxy-2,2-difluoroxylose 1-[4-hydroxy-5-(2-iodovinyl)-2-oxo-1H-pyrimidin-1-yl]-2-desoxy-2,2-difluoroxylose 1-[4-amino-5-(2-chlorovinyl)-2-oxo-1H-pyrimidin-1-yl]-2-desoxy-2,2-difluoroxylose 1-(2-amino-6-oxo-1H,9H-purin-9-yl)-2-desoxy-2,2-difluoroxylose 1-(6-amino-9H-purin-9-yl)-2-desoxy-2,2-difluoroxylose It will be understood that the reactions in which the novel 2-desoxy-2,2-difluorocarbohydrate of this invention is coupled with the bases are frequently of a nature such that the hydroxy groups must be protected to keep them from reacting with the base, or being decomposed in some manner. The protecting groups are chosen from the groups used in synthetic organic chemistry for the purpose. Chemists are accustomed to choosing groups which can be efficiently placed on hydroxy groups, and which can be easily removed when the reaction is complete. Suitable groups are described in standard textbooks, such as Chapter 3 of *Protective Groups in Organic Chemistry*, McOmie, Ed., Plenum Press, N.Y. (1973); and Chapter 2 of *Protective Groups in Organic Synthesis*, Greene, John Wiley & Sons, N.Y. (1981).

For example, hydroxy-protecting groups include such as formyl, 2-chloroacetyl, benzyl, diphenylmethyl, triphenylmethyl, 4-nitrobenzyl, phenoxycarbonyl, t-butyl, methoxymethyl, tetrahydropyranyl, allyl, tetrahydrothienyl, 2-methoxyethoxymethyl, methoxyacetyl, phenoxyacetyl, isobutyryl, ethoxycarbonyl, benzyloxycarbonyl and the like. Silyl hydroxy-protecting groups are often particularly convenient, because most of them are easily cleaved by contact with water or an alcohol. Such groups include especially trimethylsilyl, as well as isopropyldimethylsilyl, methyldiisopropylsilyl, triisopropylsilyl and the like. The t-butyldimethylsilyl group is a special case and is preferred as the protecting group in this synthesis; it is more difficultly cleaved and requires a reagent such as a hydrohalic acid to remove it from the hydroxy groups.

Ribose or xylose has a hydroxy group at the 1-position of its ring. In order to react the carbohydrate of this invention with the base, to form the antiviral compounds of this invention, it is necessary to place a leaving group at the 1-position. The leaving groups used are typical of those used commonly in organic synthesis. The preferred leaving groups are sulfonates, of which the most preferred is methanesulfonate; other typical leaving groups such as toluenesulfonate, ethanesulfonate, isopropanesulfonate, 4-methoxybenzenesulfonate, 4-nitrobenzenesulfonate, 2-chlorobenzenesulfonate, chloro and bromo may be used.

The following group of representative 2-desoxy-2,2-difluorocarbohydrates of the present invention are mentioned to assure the reader's understanding.

2-desoxy-2,2-difluororibose
3,5-bis(trimethylsilyloxy)-2-desoxy-2,2-difluororibose
3,5-dibenzyloxy-2-desoxy-2,2-difluororibose
3,5-bis(chloroacetoxy)-2-desoxy-2,2-difluororibose
3,5-bis(2-chlorobenzyloxy)-1-methanesulfonyloxy-2-desoxy-2,2-difluororibose
3,5-bis(4-nitrobenzyloxy)-1-(4-toluenesulfonyloxy)-2-desoxy-2,2-difluororibose
1-chloro-3,5-bis(phenoxyacetoxy)-1,2-desoxy-2,2-difluoroxylose
1-(2,4-dibromophenylsulfonyloxy)-3,5-bis(2,2-dimethylpropionyloxy)-2-desoxy-2,2-difluoroxylose
3,5-bis(benzoyloxy)-1-(o-toluenesulfonyloxy)-2-desoxy-2,2-difluoroxylose
1-bromo-3,5-bis(methoxycarbonyloxy)-1,2-desoxy-2,2-difluoroxylose
3,5-bis(allyloxycarbonyloxy)-1-chloro-1,2-desoxy-2,2-difluoroxylose
3,5-bis(benzyloxycarbonyloxy)-2-desoxy-2,2-difluoroxylose
1-bromo-3,5-bis(4-nitrobenzyloxycarbonyloxy)-1,2-desoxy-2,2-difluoroxylose
1-bromo-3,5-bis(tetrahydrothienyloxy)-1,2-desoxy-2,2-difluororibose
1-bromo-3,5-bis(isopropyldimethylsilyloxy)-1,2-desoxy-2,2-difluororibose
1-(2-chlorophenylsulfonyloxy)-3,5-bis(methoxymethoxy)-2-desoxy-2,2-difluororibose
3,5-bis(benzyloxymethoxy)-2-desoxy-2,2-difluororibose
1-(4-nitrophenylsulfonyloxy)-3,5-bis(trityloxy)-2-desoxy-2,2-difluororibose
3,5-bis(allyloxy)-1-chloro-1,2-desoxy-2,2-difluororibose
2-desoxy-2,2-difluoroxylose
3,5-bis(trimethylsilyloxy)-2-desoxy-2,2-difluoroxylose
3,5-dibenzyloxy-2-desoxy-2,2-difluoroxylose
3,5-bis(chloroacetoxy)-2-desoxy-2,2-difluoroxylose
3,5-bis(2-chlorobenzyloxy)-1-methanesulfonyloxy-2-desoxy-2,2-difluoroxylose
3,5-bis(4-nitrobenzyloxy)-1-(4-toluenesulfonyloxy)-2-desoxy-2,2-difluoroxylose
1-bromo-3,5-bis(tetrahydrothienyloxy)-1,2-desoxy-2,2-difluoroxylose
1-bromo-3,5-bis(isopropyldimethylsilyloxy)-1,2-desoxy-2,2-difluoroxylose
3,5-bis(t-butyldiphenylsilyloxy)-2-desoxy-2,2-difluororibose
3,5-bis(formyloxy)-1-isopropylsulfonyloxy-2-desoxy-2,2-difluororibose
3,5-bis(trichloroacetoxy)-1-methanesulfonyloxy-2-desoxy-2,2-difluororibose
1-chloro-3,5-bis(phenoxyacetoxy)-1,2-desoxy-2,2-difluororibose
1-(2,4-dibromophenylsulfonyloxy)-3,5-bis(2,2-dimethylpropionyloxy)-2-desoxy-2,2-difluororibose
3,5-bis(benzoyloxy)-1-(o-toluenesulfonyloxy)-2-desoxy-2,2-difluororibose
1-bromo-3,5-bis(methoxycarbonyloxy)-1,2-desoxy-2,2-difluororibose
1-(2-chlorophenylsulfonyloxy)-3,5-bis(methoxymethoxy)-2-desoxy-2,2-difluoroxylose
3,5-bis(benzyloxymethoxy)-2-desoxy-2,2-difluoroxylose
1-(4-nitrophenylsulfonyloxy)-3,5-bis(trityloxy)-2-desoxy-2,2-difluoroxylose
3,5-bis(allyloxy)-1-chloro-1,2-desoxy-2,2-difluoroxylose
3,5-bis(t-butyldiphenylsilyloxy)-2-desoxy-2,2-difluoroxylose
3,5-bis(formyloxy)-1-isopropylsulfonyloxy-2-desoxy-2,2-difluoroxylose
3,5-bis(trichloroacetoxy)-1-methanesulfonyloxy-2-desoxy-2,2-difluoroxylose
3,5-bis(allyloxycarbonyloxy)-1-chloro-1,2-desoxy-2,2-difluororibose
3,5-bis(benzyloxycarbonyloxy)-2-desoxy-2,2-difluororibose
1-bromo-3,5-bis(4-nitrobenzyloxycarbonyloxy)-1,2-desoxy-2,2-difluororibose The carbohydrates are prepared by a process beginning with the reaction of a D-glyceraldehyde ketonide of the formula

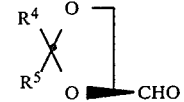

wherein $R^4$ and $R^5$ are independently $C_1$-$C_3$ alkyl, with a $C_1$-$C_4$ alkyl bromodifluoroacetate, preferably the ethyl ester.

The preferred glyceraldehyde ketonide is the acetonide wherein $R^4$ and $R^5$ are both methyl, which was first published by Fischer and Baer, *Helv. Chim. Acta.* 17, 622 (1934). Ethyl bromodifluoroacetate was first prepared by Morel and Dawans, Tet. 33, 1445 (1977). The reaction of the ketonide and the haloacetate is carried out in the presence of an activated metal such as magnesium or preferably, zinc. The activation is most easily obtained by applying ultrasonic energy to the reaction mixture. Activation by that means compensates for the presence of a small amount of water in the reaction mixture, avoiding the necessity to maintain anhydrous conditions, and also avoids the necessity to prepare and carefully store activated metals. However, the metal may be activated by the customary methods used in the art if desired. Approximately an equimolar amount of metal is the most advantageous amount.

The reaction has been performed in ethers such as tetrahydrofuran and diethyl ether, at moderate temperatures. However, other organic solvents which are inert to the conditions may be used, including halogenated alkanes such as chloroform, dichloromethane, trichloroethane and the like, and aromatics including such solvents as benzene, toluene and the xylenes. Temperatures in the range of from about ambient temperature to about 100° are convenient; temperatures from about the ambient temperature to about 80° are preferred. Economically acceptable yields have been obtained in reaction times in the range of from a few minutes to a few hours. It should be noted that the reaction is exothermic, and the mixture may therefore need to be cooled, not heated, depending on the scale of the reaction and the rate at which the reactants are added.

The product of the first reaction is an alkyl 3-dioxolanyl-2,2-difluoro-3-hydroxypropionate of the formula

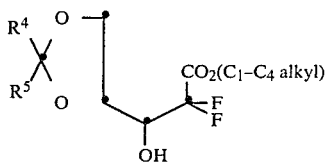

It appears that the ratio of the 3-R-hydroxy intermediate to its 3-S-hydroxy enantiomer is about 3:1. The 3-R-hydroxy enantiomer has the proper stereochemistry to yield ribose in the natural configuration, and so it is the desired enantiomeric product of the first step. The 3-R-hydroxy enantiomer can be cleanly separated from the 3-S-enantiomer by chromatography on silica gel, eluting with chloroform containing 0.5% methanol.

The hydroxypropionate, in either form, is hydrolyzed under very mild conditions to form the lactone form of the carbohydrate, of the formula

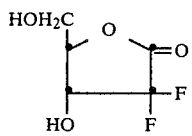

It has been found that proper control of the hydrolysis step will cleave the ketonide function and, unexpectedly, will also cleave the ester group, providing the lactone in a single step. The hydrolysis reagent is preferably a mildly acidic ion exchange resin, of which Dowex 50W-X12 (Dow Chemical Company) is most highly preferred. It is possible to carry out the process with other mild hydrolytic reagents, although it is possible that larger amounts of by-products may be obtained. For example, aqueous acetic acid, or other relatively strong acids such as propionic acid, formic acid, chloroacetic acid, oxalic acid and the like, may be used for the hydrolysis.

The hydroxy groups of the lactone should be protected before its keto oxygen is reduced. The usual reaction conditions are used, depending on the nature of the protecting groups which may be chosen. For example, the t-butyldimethylsilyl group is most conveniently provided in the form of its trifluoromethanesulfonate, and the protection reaction is carried out in the presence of a base such as lutidine, pyridine and the like. Acyl protecting groups such as acetyl, benzoyl and the like are provided by reacting the lactone with an acylating agent such as an acyl chloride, bromide, cyanide or azide, or with an appropriate anhydride. The reactions are conveniently carried out in a basic solvent such as pyridine, quinoline or isoquinoline, or in a tertiary amine solvent such as triethylamine, tributylamine, methylpiperidine and the like. The reaction may also be carried out in an inert solvent, to which an acid scavenger, such as a tertiary amine, has been added. Acylation catalysts such as 4-dimethylaminopyridine or 4-pyrrolidinopyridine may be used in the reaction, if desired. The acylation reactions which provide protecting groups on the hydroxy groups are carried out at moderate temperatures in the range of from −25° to 100°. Such acylations may also be performed by acid-catalyzed reactions of the appropriate carboxylic acids, in inert organic solvents or neat. Acid catalysts such as sulfuric acid, polyphosphoric acid, methanesulfonic acid and the like are used.

Acyl protecting groups may also be provided by forming an active ester of the appropriate acid, such as the esters formed by such known reagents as dicyclohexylcarbodiimide, acylimidazoles, nitrophenols, pentachlorophenol, N-hydroxysuccinimide and 1-hydroxybenzotriazole.

Protecting groups of the ether type are placed by reacting the lactone with, for example, an appropriate diazo compound, such as diazomethane, phenyldiazomethane or a silyldiazomethane. Such reactions are commonly and effectively carried out in solvents including esters such as ethyl acetate, halogenated solvents including dichloromethane and chloroform, and ethers including diethyl ether and tetrahydrofuran. The process is usually carried out at low temperatures from about −50° to about 0°. Such etherforming reactions may also be carried out with the assistance of reagents such as trimethyloxosulfonium hydroxide, trimethylsulfonium hydroxide and trimethylselenonium hydroxide, in solvents such as dimethylsulfoxide, dimethylformamide, hexamethylphosphoramide, acetone, acetonitrile and the like.

The silyl protecting groups discussed above are placed on the hydroxy groups by the conventional methods, such as by reaction with the appropriate silylcarboxamide or bis(substituted-silyl)carboxamide, or an appropriately substituted silazane. Suitably substituted silyl methanesulfonates, toluenesulfonates and the like are also useful. An equivalent of a base is usually necessary in the reaction mixture, unless a basic solvent such as is discussed above is used as the reaction medium.

When the hydroxy groups have been protected, the keto oxygen of the lactone is reduced to the alcohol, forming the protected 2-desoxy-2,2-difluororibose or xylose of this invention. The most preferred reducing agent is diisobutyl aluminum hydride, used at a low temperature in the range of about −100° to −20°. It is necessary to carry out the reduction very carefully, in order to avoid reducing conditions so vigorous that the ring is opened at the oxygen atom. Other metal hydrides, such as the widely used lithium aluminum hydride, can also be used for the reduction, but it is necessary to keep the temperature quite low and to assure that the hydride is destroyed before the temperature is allowed to rise toward ambient. Accordingly, a solvent with a very low freezing point must be used in the reduction step. Toluene is convenient; other solvents can of course be used, including lower alkanols, especially ethanol, ethers such as diethyl ether, and the like.

An appropriate leaving group must be placed at the 1-position of the carbohydrate, in order to obtain efficient reaction with the base. The preferred leaving group is methanesulfonyl, which is readily provided by reaction with methanesulfonyl chloride in the presence of an equivalent amount of a suitable acid scavenger such as triethylamine and the like. Other sulfonyl leaving groups are provided in the same way by reaction with the appropriate sulfonyl halide.

When a chloro or bromo leaving group is to be used, it is frequently convenient first to make the 1-acetate derivative, as by reaction with acetic anhydride, or another source of acetyl groups, in the presence of an equivalent or more of an acid scavenger. Then the acetate group is displaced with gaseous hydrogen bromide or hydrogen chloride, at a low temperature such as about −50° to about 0°. Since the gaseous hydrogen halide may tend to remove the protecting groups, especially silyl protecting groups, it is necessary to operate this step at quite a low temperature and to add the hydrogen halide slowly in small increments.

The bases used to form the antiviral compounds of the present invention are commonly known to organic chemists, and no discussion of their synthesis is necessary. However, the primary amino groups which are present on some of the bases should be protected before the base is coupled with the carbohydrate. The usual amino-protecting groups are used, including silyl groups such as have been discussed, as well as such typical groups as t-butoxycarbonyl, benzyloxycarbonyl, 4-methoxybenzyloxycarbonyl, 4-nitrobenzyloxycarbonyl, formyl, acetyl, and the like.

It is often advisable to convert keto oxygen atoms on the bases to the enol form, in order to make the base more highly aromatic and thereby allow more ready attack of the base by the carbohydrate. It is most convenient to enolize the oxygens by providing silyl protecting groups for them. The usual silyl protecting groups as discussed above are used for this purpose, also.

The reaction between the protected carbohydrate and the base is preferably carried out neat at an elevated temperature in the range of from about 50° to about 200°. It is possible, however, to use relatively high-boiling solvents for the reaction, such as dimethylformamide, dimethylacetamide, hexamethylphosphoramide and the like. However, if the coupling reaction is carried out under elevated pressure, to avoid distillation of a low-boiling solvent, any convenient inert reaction solvent can be used.

The coupling reaction may be done at low temperatures if a reaction initiator, such as a trifluoromethanesulfonyloxysilane, is used. The usual inert reaction solvents, as discussed above, may be used at temperatures in the range of from about ambient to about 100°.

The final step of the reaction sequence is the removal of the protecting groups. Most silyl protecting groups are easily cleaved by contact with water or an alcohol. The t-butyldimethylsilyl protecting group requires acid conditions, such as contact with gaseous hydrogen halide, for its removal.

Acyl protecting groups are removed by simple hydrolysis with strong or moderately strong bases, such as alkali metal hydroxides, at temperatures from about the ambient temperature to about 100°. At least one equivalent of base is needed for each protecting group, of course. Such hydrolyses are conveniently carried out in hydroxylic solvents, especially aqueous alkanols. The reactions may be also carried out, however, in any convenient solvent, such as polyols including ethylene glycol, ethers such as tetrahydrofuran and the like, ketones such as acetone and methyl ethyl ketone and other polar solvents such as dimethylsulfoxide. The cleavage of acyl protecting groups may also be performed with other bases, including, for example, sodium methoxide, potassium t-butoxide, hydrazine, hydroxylamine, ammonia, alkali metal amides and secondary amines such as diethylamine and the like. The acyl protecting groups can also be removed with acid catalysts, such as methanesulfonic acid, hydrochloric acid, hydrobromic acid, sulfuric acid, or with acidic ion exchange resins. It is preferred to carry out such hydrolyses at a relatively high temperature, such as the reflux temperature of the mixture, but temperatures as low as ambient may be used when particularly strong acids are used.

The removal of protecting groups which are ethers is carried out by known methods, for example, with ethanethiol and aluminum chloride.

None of the reaction steps require unusual excesses of the reactants. As usual in organic syntheses, it is advisable and economical to use a moderate excess, in the range of 1.05X to 2X, for example, of the cheaper reagents to assure that the costlier ones are consumed.

The following preparations and examples further illustrate the synthesis of the compound of the present invention.

PREPARATION 1 ethyl 2,2-difluoro-3-hydroxy-3-(2,2-dimethyldioxolan-4-yl)propionate

To 10.2 g. of activated zinc was added a small portion of a solution consisting of 31.8 g. of ethyl bromodifluoroacetate and 22.6 g. of 4-formyl-2,2-dimethyldioxolane in 53 ml. of tetrahydrofuran and 53 ml. of diethyl ether. Care was taken to exclude water from the reaction mixture. The solution began to reflux as soon as the first addition to the activated zinc was made. The remainder of the solution was added dropwise at a rate to maintain gentle reflux throughout the addition time of about 30 minutes. The mixture was then stirred under gentle reflux for 30 minutes more. The reaction mixture was poured into 200 ml. of 1N hydrochloric acid and 200 g of ice, and the mixture was stirred until all of the ice had melted. The aqueous mixture was then extracted four times with 70 ml. portions of diethyl ether, and the organic layers were combined and washed with 50 ml. of saturated aqueous sodium chloride and with 50 ml. of saturated aqueous sodium bicarbonate, dried over magnesium sulfate and evaporated under vacuum to obtain 26 g. of light yellow oil. The crude product was chromatographed on a 1000 g. silica gel column, eluting with chloroform containing 0.5% methanol to separate the major 3-R-hydroxy product from the minor 3-S-hydroxy product. The ratio of amounts of the two products was about 3:1; the minor product came off the column first.

Evaporation of the fractions containing the 3-R-hydroxy product provided 12.6 g. of the product in substantially pure form. It was identified by mass spectrometry, showing a fragment of weight 239, which agrees with the molecular weight of the desired product less a methyl group which was lost from the acetonide function in the spectrometric measurement. A nuclear magnetic resonance analysis of the 3-R-hydroxy product on a 90 mHz instrument in $CDCl_3$ showed features at $\delta = 3.94-4.45$ (m, 5H); 3.14 (d, J=4.5 Hz, 1H); 1.2–1.47 (m, 9H).

Analysis by the same nmr procedure of the 3-S-hydroxy product, of which 4.68 g. was obtained by evaporation of the chromatography fractions containing it, showed features at 3.75–4.47 (m, 6H); 2.95 (d, J=8 Hz, 1H); 1.25–1.5 (m, 9H).

PREPARATION 2

2-desoxy-2,2-difluoro-1-oxoribose

Fifty g. of the 3-R-hydroxy product obtained from a synthesis similar to that of Preparation 1 above was dissolved in 500 ml. of methanol and 250 ml. of water, and 250 g. of Dowex 50W-X12 resin was added. The mixture was stirred at ambient temperature for 4 days, and the mixture was then filtered through a pad of diatomaceous earth filter aid. The filtrate was evaporated to dryness under vacuum to obtain 33.0 g. of the desired product, which was identified by nmr analysis on a 90 mHz instrument in $CD_3OD$: $\delta = 3.6–4.6$ (series of m, 4H); 4.8 (bs, 2H).

PREPARATION 3

3,5-bis(t-butyldimethylsilyloxy)-2-desoxy-2,2-difluoro-1-oxoribose

To 13 g. of the product obtained in Preparation 2 above was added 60 ml. of dichloromethane, 22.5 ml. of 2,6-lutidine and 48.2 ml. of trifluoromethylsulfonyloxy t-butyldimethylsilane under nitrogen with mild cooling to keep the temperature below 25°. Within 15 minutes after combining the reagents, the reaction became quite exothermic and the mixture became thin and easily stirred. The mixture was stirred overnight. The mixture was diluted with 150 ml. of ethyl acetate, and was washed successively with 40 ml. of 1N hydrochloric acid, 40 ml. of saturated aqueous sodium bicarbonate and 40 ml. of saturated aqueous sodium chloride. It was then dried over magnesium sulfate and evaporated to dryness under vacuum to obtain 32.1 g. of crude product, which was chromatographed on 260 g. of 100-mesh silica gel, eluting with 10:1 chloroform:diethyl ether. The fractions which contained the desired product were combined and evaporated under vacuum to obtain 7.8 g. of pure product. Other fractions were combined and evaporated to obtain an additional 10 g. of impure product, which was not further purified. Analysis of the pure product gave the following results: IR (neat) 1820 cm.$^{-1}$; nmr (CDCl$_3$, 90 MHz) $\delta = 0.1–0.22$ (m, 12H); 0.83–0.98 (m, 18H); 3.63–4.7 (series of m, 4H); mass spec. m/e = 339 = P-t-butyl.

EXAMPLE 1

3,5-bis(t-butyldimethylsilyl)-2-desoxy-2,2-difluororibose

A 10.3 g. portion of 3,5-bis(t-butyldimethylsilyloxy)-2-desoxy-2,2-difluoro-1-oxoribose, obtained from preparations similar to that of Preparation 3 above, was dissolved in 120 ml. of anhydrous toluene and cooled to −84°. To the solution was added 26 g. of diisobutyl aluminum hydride, added over a period of 20 minutes with constant stirring. The reaction mixture was held below −65° at all times. Two hours after the first addition of hydride, the reaction mixture was quenched with methanol at −20°, additional cold methanol was added until no more gassing occurred. The mixture was then allowed to warm slowly to ambient temperature, and was washed with 100 ml. of 0.1N hydrochloric acid. The aqueous layer was then washed with 100 ml. of diethyl ether, and then three times with 50 ml. portions of diethyl ether. The organic layers were combined, washed with 100 ml. of saturated aqueous sodium bicarbonate, dried over magnesium sulfate and evaporated under vacuum to dryness to obtain 8.2 g. of the desired product in crude form.

This material may be chromatographed, if necessary, on silica gel (25 g. silica/1 g. of crude product) using 100% dichloromethane for elution. nmr (CDCl$_3$, 90 MHz) $\delta = 0.1–0.24$ (m, 12H); 0.85–1.0 (m, 18H); 3.33–4.63 (series of m, 5H); 5.0–5.27 (dd, 1H); mass spec. m/e = 341 = P-t-butyl; $[\alpha]_D^{25°} = +25.1°$.

EXAMPLE 2

3,5-bis(t-butyldimethylsilyloxy)-1-methanesulfonyloxy-2-desoxy-2,2-difluororibose An 0.5 g. portion of 3,5-bis(t-butyldimethylsilyloxy)-2-desoxy-2,2-difluororibose was dissolved in 5 ml. of anhydrous dichloromethane and 0.17 g. of triethylamine. To the solution was added, with mild cooling, 0.11 ml. of methanesulfonyl chloride. After three hours of stirring under nitrogen at about 25°, the mixture was evaporated under vacuum, and the residue was taken up in 10 ml. of ethyl acetate. The solution was extracted with 3 ml. of saturated aqueous sodium bicarbonate, and then successively with 3 ml. of 1N hydrochloric acid, 3 ml. of water and 3 ml. of saturated aqueous sodium chloride. The organic solution was then dried over sodium sulfate and concentrated under vacuum to obtain 0.59 g. of the desired product, nmr (CDCl$_3$, 90 MHz) $\delta$ 0.05–0.16 (m, 12H); 0.78–0.90 (m, 18H); 3.0 (s, 3H); 3.63–4.59 (series of m, 4H); 5.67–5.9 (dd, 1H); mass spec. m/e = 419 = P-t-butyl.

EXAMPLE 3

1-(5-methyl-2,4-dioxo-1H,3H-pyrimidin-1-yl)-1,2-desoxy-2,2-difluororibose

Under nitrogen, to 2.59 g. of 3,5-bis(t-butyldimethylsiloxy)-1-methanesulfonyloxy-2-desoxy-2,2-difluororibose was added 1.60 g. of 5-methyl-2,4-bis(trimethylsilyloxy)pyrimidine and 45 ml. of dry 1,2-dichloroethane. To this mixture was added 1.45 g. of trifluoromethanesulfonyloxytrimethylsilane, and the clear solution was stirred under reflux for about 2–3 hours. The reaction was then cooled to ambient temperature and 1.35 ml. of methanol were added and the suspension was stirred for 30 minutes. The precipitate was filtered and the filtrate was reduced to one-half its volume under vacuum and then diluted with an equal volume of dichloromethane. The solution was washed with saturated aqueous sodium bicarbonate and then with saturated aqueous sodium chloride, and dried over anhydrous sodium sulfate. The solution was filtered and the filtrate was saturated with anhydrous hydrogen bromide. The reaction mixture was stirred for 30 minutes and was then concentrated under vacuum. The residue was dissolved in methanol and the solution was evaporated to dryness under vacuum. The residue was dissolved in water and the solution was extracted twice with diethyl ether. The water layer was then evaporated to dryness. The residue was taken up in ethanol and evaporated repeatedly to azeotrope off all water. One g. of crude product was obtained, and was chromatographed on 30 g. of Woelm silica gel (70–150 mesh), eluting with ethyl acetate to yield 0.76 g. of desired product. It was further purified by recrystallization from ethyl acetate to obtain 0.37 g. of white crystalline product. nmr (CD$_3$OD 90 MHz) $\delta$ 1.93 (s, 3H); 3.5–4.67 (series of m, 4H); 4.83 (bs, 3H); 6.3 (t, J = 9Hz, 1H); 7.47 (m, 1H); mass spec m/e = 278 = Parent.

EXAMPLE 4

1-(5-methyl-2,4-dioxo-1H,3H-pyrimidin-1-yl)-1,2-desoxy-2,2-difluororibose

A 5.4 g. portion of 3,5-bis(t-butyldimethylsilyloxy)-1-methanesulfonyloxy-2-desoxy-2,2-difluororibose and 5.4 g. of 5-methyl-2,4-bis(trimethylsilyloxy)pyrimidine were combined and heated under nitrogen with stirring at 100° for one hour, and then at 150° for one hour. The mixture was then cooled to ambient temperature and diluted with 25 ml. of water and 10 ml. of methanol. The slurry was filtered over a diatomaceous earth filter pad, and the cake was washed with acetone. The combined filtrate was evaporated under vacuum to obtain 5.3 g. of an oily residue. The residue was dissolved in 10 ml. of acetone and loaded on a 4.5 cm. column packed with 80 g. of silica gel. It was eluted with 15:1:1 dichloromethane:methanol:triethylamine.

The first 100 ml. of eluent was discarded, and the next 300 ml. was evaporated under vacuum to obtain 4.1 g. of syrupy crude product, which was dissolved in 40 ml. of acetone. Hydrogen chloride was bubbled through the solution for 1 hour, and then hydrogen bromide was bubbled through for 1 hour more. The solution was then evaporated at 62° to obtain 4.4 g. of oily dark product.

The above product was dissolved in 10 ml. of warm 3:1 dichloromethane:acetic acid, and loaded on a 4.5 cm. column packed with 45 g. of silica gel. The eluent used for the first 1000 ml. was 3:1 dichloromethane:acetic acid, and thereafter it was acetic acid alone. Most of the desired product was in the fractions between 1000 and 1400 ml. off the column, as determined by thin layer chromatography on silica gel using 15:1 dichloromethane:methanol. Those fractions were combined and evaporated under vacuum, and the residue was taken up in 15 ml. of cold acetone and filtered. The filtrate was stripped under vacuum to obtain an oil, which was dissolved in 5 ml. of acetone and chromatographed over 20 g. of silica gel with 15:1 dichloromethane:methanol. The product-containing fractions were combined and evaporated under vacuum to obtain 300 mg. of a semi-solid. That product was taken up in 5 ml. of acetone and filtered, and the filtrate was evaporated under vacuum to obtain 230 mg. of light brown semi-solid. It was dissolved in 10 ml. of saturated aqueous sodium bicarbonate, and the solution was extracted twice with 15 ml. portions of diethyl ether. The aqueous phase was then evaporated under vacuum, the residue was slurried in acetone and filtered, and the filtrate was evaporated under vacuum to obtain 140 mg. of the desired product as a tan viscous oil.

The antiviral effect of the compounds of this invention has been shown by a proven in vitro test, which was carried out as follows. A representative compound, that of Examples 3 and 4 above, was tested, and is referred to in the following description by the code term "DFAT".

Test 1

African green monkey kidney cells (BSC-1) were grown in 25 cm.$^2$ Falcon flasks at 37° in medium 199 with 5 percent inactivated fetal bovine serum (FBS), penicillin (150 units/ml.) and streptomycin (150 mcg./ml.). When confluent monolayers were formed, the supernatant growth medium was removed and 0.3 ml. of an appropriate dilution of pseudorabies virus or *Herpes simplex* virus, type I, was added to each flask. After adsorption for one hour at room temperature, the virus infected cell sheet was overlaid with a medium comprising one part 1 percent Ionagar No. 2 and one part double strength medium 199 with FCS (fetal calf serum), penicillin, and streptomycin and also containing crude DFAT at concentrations ranging from 100 to 0.39 micrograms per milliliter (mcg./ml.). A flask containing no DFAT served as a control. The stock solution of DFAT was made up in dimethylsulfoxide at a concentration of $10^4$ mcg./ml. The flasks were incubated for 72 hours at 37°. Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the compound was expressed as percentage plaque inhibition.

The results of these evaluations are reported below in Tables 1 and 2.

TABLE 1

Percent Plaque Inhibition at Specified Mcg./Ml. of DFAT Concentration in Agar Overlay
Herpes simplex, type I

| 100 | 50 | 25 | 12.5 | 6.25 | 3.12 | 1.56 | 0.78 | 0.39 |
|---|---|---|---|---|---|---|---|---|
| 96% | 72% | 53% | 35% | 15% | 12% | 0 | 8% | 4% |

TABLE 2

Percent Plaque Inhibition at Specified Mcg./Ml. of DFAT Concentration in Agar Overlay
Pseudorabies Virus

|  | 100 | 50 | 25 | 12 | 6 | 3 |
|---|---|---|---|---|---|---|
| DFAT | 23% | 18% | 15% | 12% | 6% | 5% |

The antiviral nucleosides of the present invention are used for the treatment of viral infections in the manner usual in the treatment of such pathologies. The compounds are effective for the treatment of viral infections in general, and most particularly in the treatment of infections caused by viruses of the herpes genus.

The compounds are effectively administered orally, topically or parenterally. In general, dosage rates in the range of from about 5 mg./kg. to about 500 mg./kg. are useful. It is more preferred to administer rates in the range of from about 10 mg./kg. to about 100 mg./kg.

The compounds are usually used in medicine in the form of one of the pharmaceutical compositions of the present invention, which compositions are novel and important because of the presence of the novel nucleosides in them. The formulation of the compositions is conventional, and follows the usual practices of pharmaceutical chemists. When a nucleoside of the present invention is to be administered topically, it is formulated as a topical composition, such as a cream or ointment to be rubbed into the affected tissue. Creams are emulsions of an oily phase and an aqueous phase, in which the nucleoside is dissolved or suspended. Ointments are greasy or waxy compositions, in which the nucleoside may be soluble but may be suspended, if it is insoluble at the desired concentration.

Parenteral compositions are preferably formulated in such a way that the nucleoside can be dissolved for injection, but most of the nucleosides are by no means highly water-soluble. Thus, it is more common for a parenteral product to be formulated as a dried powder of the nucleoside and physiologically-acceptable suspending agents, such as starch, sugar and the like, to which sterilized water is added to form a suspension to be injected. Parenteral compositions can be formulated in aqueous bases containing moderate amounts of physiologically-acceptable solvents, such as propylene glycol and the like, and such compositions may be capable of dissolving the present nucleosides at acceptable concentrations.

A great many types of orally administered compositions are in common use, including unit dosage forms such as tablets and capsules, and liquid dosage forms such as suspensions. In general, unit dosage forms are preferred in pharmacy and are formulated in such a way as to provide the usual dose in one or a small number of tablets or capsules. The formulation of tablets, making use of appropriate lubricants, binding agents and disintegration agents, is and long has been thoroughly understood by pharmaceutical chemists. The formulation of capsules involves only the dilution of the nucleoside with an appropriate proportion of an inert powdery substance, such as lactose, to provide the proper bulk to fill the desired size of capsule. The formulation of orally-administered suspensions is carried out by finely grinding the nucleoside, and intimately mixing it with a comparatively viscous aqueous-base liquid. The viscosity is adjusted by the addition of pharmaceutically-acceptable thickening or gel-forming agents including vegetable gums, chemically-modified cellulose derivatives and the like. Of course, appropriate flavors are used to make the suspensions organoleptically acceptable.

I claim:
1. A process for preparing a lactone of the formula

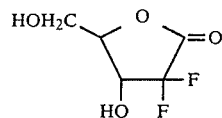

which process comprises hydrolyzing, under very mild conditions, an alkyl 3-dioxolanyl-2,2-difluoro-3-hydroxypropionate of the formula

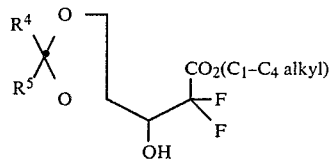

wherein $R^4$ and $R^5$ are independently $C_1$–$C_3$ alkyl.

2. A process of claim 1 wherein the propionate is a compound wherein $R^4$ and $R^5$ are methyl groups.

3. A process of claim 2 wherein the hydrolysis reagent is a mildly acidic ion exchange resin.

* * * * *

UNITED STATES PATENT AND TRADEMARK OFFICE
CERTIFICATE OF CORRECTION

PATENT NO. : 4,526,988
DATED : July 2, 1985
INVENTOR(S) : Larry W. Hertel

It is certified that error appears in the above—identified patent and that said Letters Patent is hereby corrected as shown below:

Column 2, lines 49-55; Column 7, lines 4-10 and Column 16, lines 14-20, that portion of the formula which reads

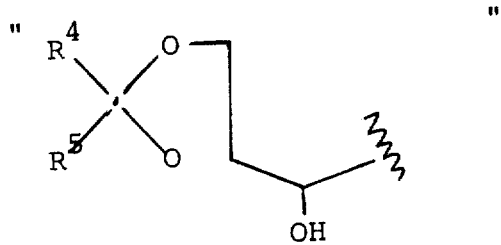

should read

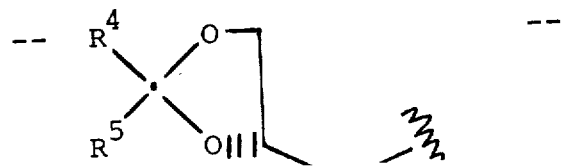

Signed and Sealed this

First Day of December, 1987

Attest:

DONALD J. QUIGG

Attesting Officer

Commissioner of Patents and Trademarks